United States Patent
Shahar et al.

(10) Patent No.: US 9,349,495 B2
(45) Date of Patent: May 24, 2016

(54) SYSTEMS AND METHODS FOR IMPROVED COLLIMATION SENSITIVITY

(71) Applicant: General Electric Company, Schenectady, NY (US)

(72) Inventors: Arie Shahar, Moshav Magshimim (IL); Avishai Ofan, Rehovot (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/258,209

(22) Filed: Apr. 22, 2014

(65) Prior Publication Data

US 2015/0302945 A1 Oct. 22, 2015

(51) Int. Cl.
*G21K 1/02* (2006.01)
*A61B 6/00* (2006.01)
*A61B 6/03* (2006.01)
*A61B 6/06* (2006.01)

(52) U.S. Cl.
CPC ............... *G21K 1/025* (2013.01); *A61B 6/037* (2013.01); *A61B 6/06* (2013.01); *A61B 6/4258* (2013.01); *A61B 6/4266* (2013.01); *A61B 6/4429* (2013.01)

(58) Field of Classification Search
CPC ........... G21K 1/025; G01T 1/249; G01T 1/29
USPC ....................................................... 250/362
See application file for complete search history.

(56) References Cited

U.S. PATENT DOCUMENTS

| 4,165,462 | A | * | 8/1979 | Macovski et al. ........ 250/363.04 |
| 6,140,650 | A | | 10/2000 | Berlad |
| 6,239,438 | B1 | | 5/2001 | Schubert |
| 6,748,044 | B2 | | 6/2004 | Sabol et al. |
| 6,943,355 | B2 | | 9/2005 | Shwartz et al. |
| 7,026,623 | B2 | | 4/2006 | Oaknin et al. |
| 7,381,959 | B2 | | 6/2008 | Manjeshwar et al. |
| 7,671,331 | B2 | | 3/2010 | Hefetz |
| 7,671,340 | B2 | * | 3/2010 | Uribe et al. ................. 250/363.1 |
| 9,029,791 | B1 | * | 5/2015 | Kovalski et al. .............. 250/369 |
| 2002/0191828 | A1 | | 12/2002 | Colbeth et al. |
| 2003/0230723 | A1 | * | 12/2003 | Garrard et al. ............. 250/363.1 |
| 2005/0145797 | A1 | | 7/2005 | Oaknin et al. |
| 2006/0004191 | A1 | * | 1/2006 | Jhiang et al. ................. 536/23.5 |
| 2006/0108532 | A1 | | 5/2006 | Ohana et al. |
| 2007/0018108 | A1 | | 1/2007 | Kitamura |
| 2008/0078937 | A1 | * | 4/2008 | Tsuchiya et al. .............. 250/366 |
| 2008/0116386 | A1 | * | 5/2008 | Wagenaar et al. ....... 250/370.09 |
| 2009/0304150 | A1 | * | 12/2009 | Metzler et al. .................. 378/62 |

(Continued)

OTHER PUBLICATIONS

Meikle et al., "Accelerated EM reconstruction in total-body PET: potential for improving tumour detectability," 1994, Physics in Medicine and Biology, vol. 39, pp. 1689-1704.

(Continued)

*Primary Examiner* — Marcus Taningco
(74) *Attorney, Agent, or Firm* — Dean D. Small; The Small Patent Law Group, LLC

(57) ABSTRACT

A collimator assembly is provided including a parallel-hole collimator and a pin-hole collimator. The parallel-hole collimator includes plural walls defining parallel holes therebetween, with the parallel holes arranged around a central opening. The pin-hole collimator includes a pin-hole formed in a body, with the pin-hole collimator disposed within the central opening.

22 Claims, 11 Drawing Sheets

(56) References Cited

U.S. PATENT DOCUMENTS

2013/0126744 A1* 5/2013 Jansen et al. ............. 250/370.08
2014/0093035 A1* 4/2014 Beekman .................... 378/37

OTHER PUBLICATIONS

Riddell et al., "Noise reduction in oncology FDG PET images by iterative reconstruction: a quantitative assessment," 2001, the Journal of Nuclear Medicine, vol. 42, No. 9, pp. 1316-1323.

Shepp et al., "Maximum likelihood reconstruction for emission tomography," 1982, IEEE Transaction on Medical Imaging, vol. MI-1, No. 2, pp. 113-121.

Park et al., "Performance of a high-sensitivity dedicated cardiac SPECT scanner for striatel uptake quantification in the brain based on analysis of projection data," Med. Phys. 40 (4), Apr. 2013.

* cited by examiner

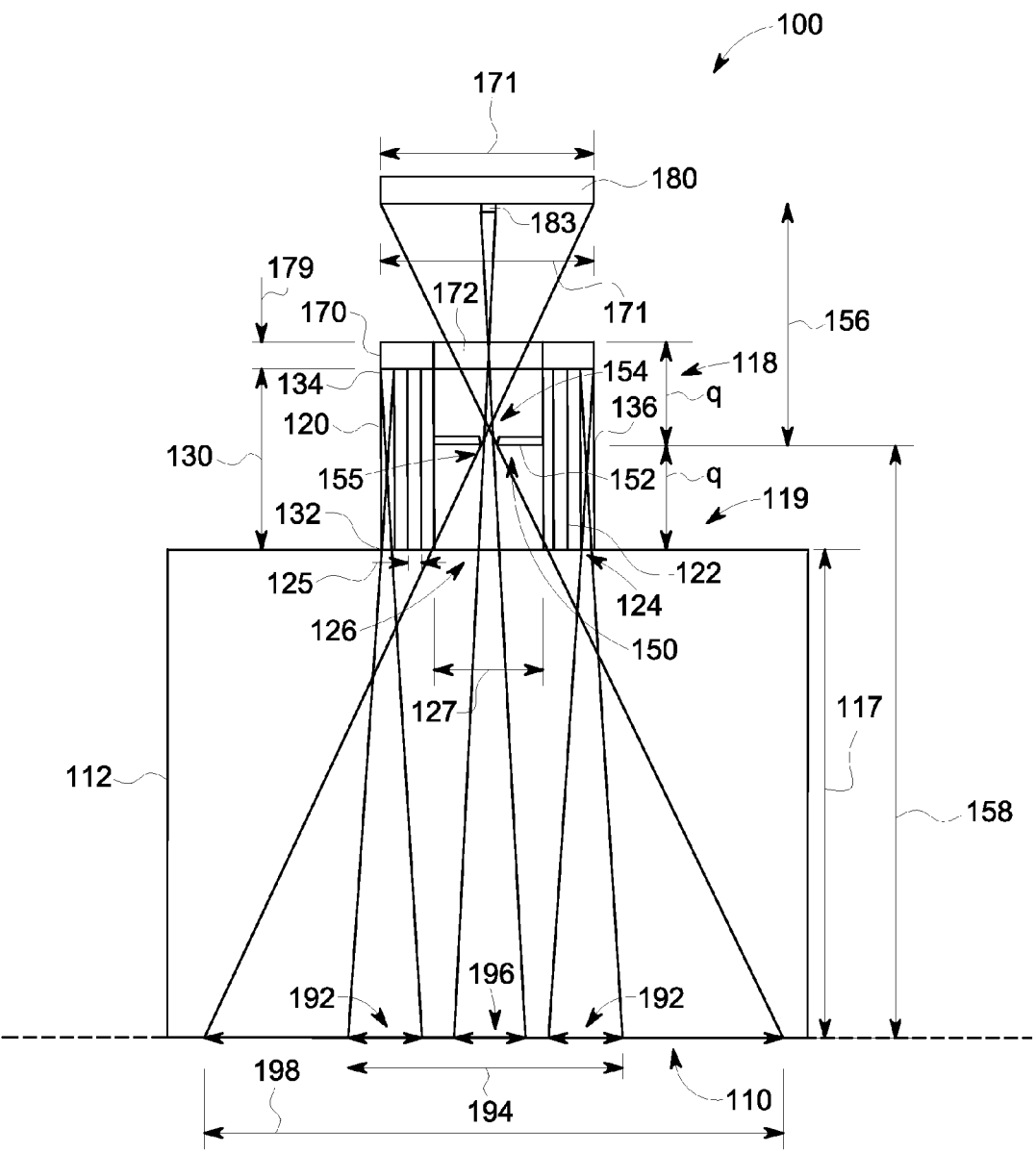
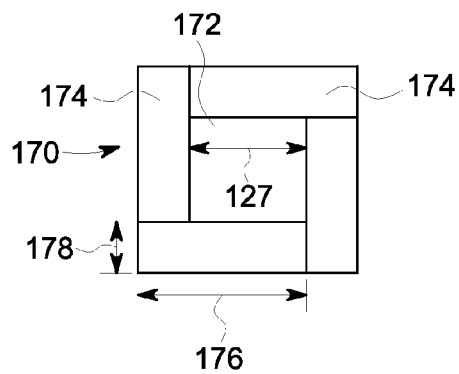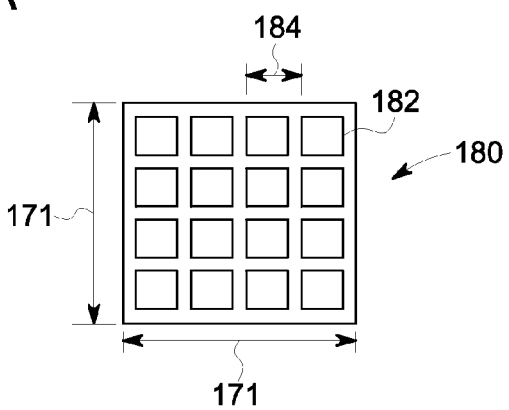
FIG. 1A
FIG. 1B
FIG. 1C

SYSTEMS AND METHODS FOR IMPROVED COLLIMATION SENSITIVITY

BACKGROUND OF THE INVENTION

The subject matter disclosed herein relates generally to apparatus and methods for diagnostic medical imaging, such as Nuclear Medicine (NM) imaging.

In NM imaging, systems with multiple detectors or detector heads may be used to image a subject, such as to scan a region of interest. For example, the detectors may be positioned adjacent the subject to acquire NM data, which is used to generate a three-dimensional (3D) image of the subject.

Single Photon Emission Computed Tomography (SPECT) systems may have moving detector heads, such as gamma detectors positioned to focus on a region of interest. For example, a number of gamma cameras may be moved (e.g., rotated) to different angular positions for acquiring image data. The acquired image data is then used to generate the 3D images.

The size of the detector heads may limit an available usable area for the placement of detectors, such as Cadmium Zinc Telluride (CZT) wafers. The sensitivity (e.g., the proportion of radiation received relative to the radiation emitted) may be limited by the size of the detector heads and/or the arrangement of CZT wafers. Conventional approaches to improving sensitivity may use thicker detectors, or detectors arranged in generally identical or similar layers stacked directly one on top of each other. Such conventional approaches may not provide a desired or required sensitivity.

BRIEF DESCRIPTION OF THE INVENTION

In one embodiment, a collimator assembly is provided including a parallel-hole collimator and a pin-hole collimator. The parallel-hole collimator includes plural walls defining parallel holes therebetween, with the parallel holes arranged around a central opening. The pin-hole collimator includes a pin-hole formed in a body, with the pin-hole collimator disposed within the central opening.

In another embodiment, a rotating head detector assembly is provided that includes an arm and a detector head. The detector head is pivotally attached to the arm and configured to be directed toward a source. The detector head includes plural nuclear medicine (NM) imaging detectors and at least one pin-hole collimator. The plural nuclear medicine (NM) imaging detectors are configured to receive radiation from the source, with each NM imaging detector positioned to receive radiation directly from the source over at least a portion of the NM imaging detector. The at least one pin-hole collimator is positioned to collimate radiation received by at least one of the NM imaging detectors.

In another embodiment, a method for forming a collimator assembly is provided. The method includes providing a parallel-hole collimator including plural walls defining parallel holes therebetween, with the parallel holes arranged around a central opening. The method also includes providing a pin-hole collimator including a pin-hole formed in a body. Further, the method includes positioning the pin-hole collimator within the central opening of the parallel-hole collimator to form the collimator assembly.

BRIEF DESCRIPTION OF THE DRAWINGS

FIGS. 1a-1c provide views of a collimator assembly in accordance with an embodiment.

DETAILED DESCRIPTION OF THE INVENTION

Figure 2:
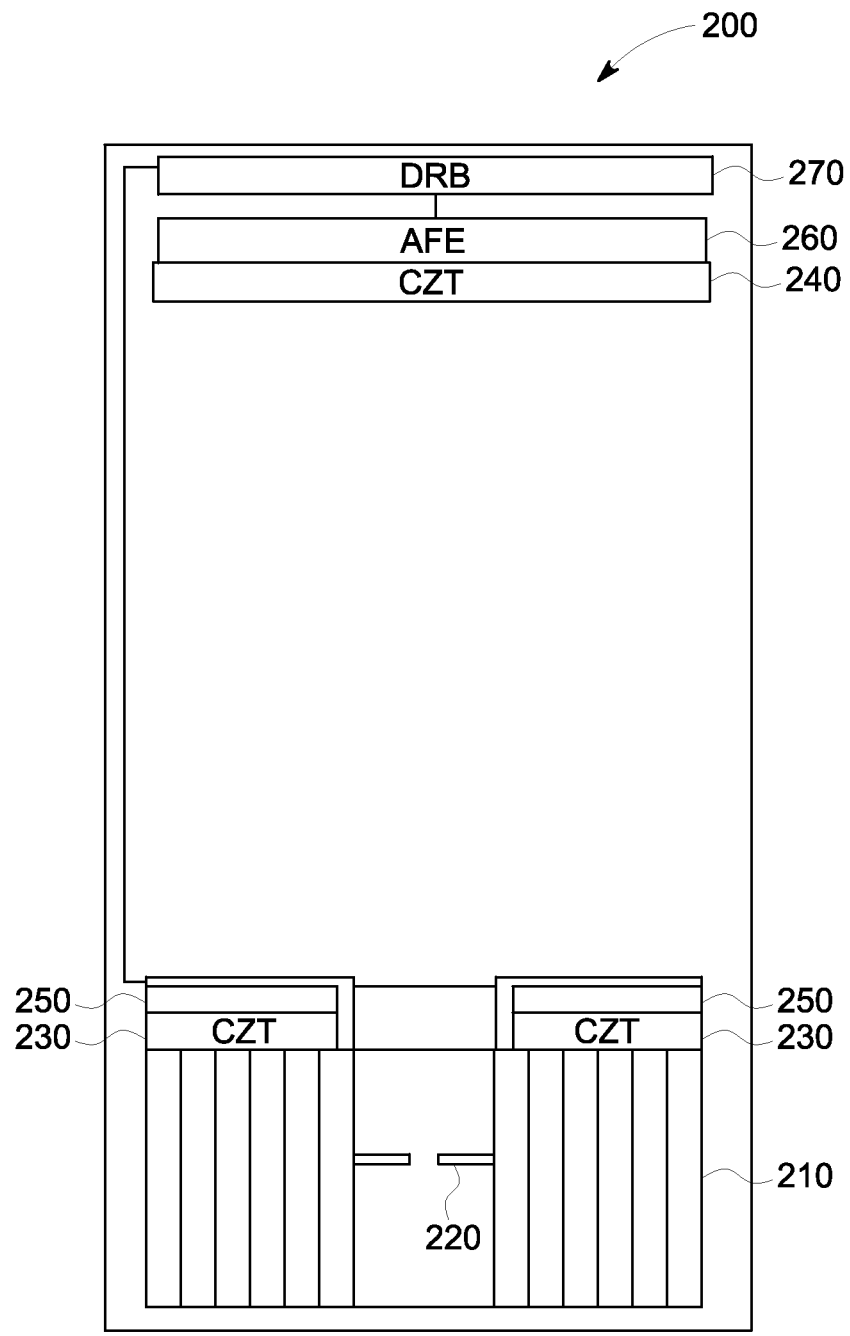
FIG. 2 is a schematic block diagram illustrating a detector assembly in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for improving the sensitivity of image acquisition, for example in Nuclear Medicine (NM) imaging applications. Various embodiments increase the sensitivity (e.g., the proportion of radiation received by detectors of the total radiation emitted toward the detectors) using standard Cadmium Zinc Telluride (CZT) detector wafers. Various embodiments may provide for an increase of 150% or more of sensitivity relative to a single CZT detector wafer. In various embodiments, two or more CZT detector wafers may be employed. For example, two detectors may be placed one above the other (e.g., with one interposed between the other and the source of emitted radiation, such as a human patient). In conventional CZT detectors using double CZT wafers, the added sensitivity is relatively modest because a large amount of the radiation is absorbed in the first CZT layer, making the second upper CZT layer inefficient. For example, because most of the possible area available for occupying detector-modules is already used in conventional approaches, only the option of adding additional CZT absorbing area along a height of a detector remains for conventional stacked approaches. However, such an arrangement is not very efficient. For example, the stopping power of a 5 mm CZT layer is about 90% for the 140 KeV energy of $^{99}$Tc isotope. Using a thicker CZT layer, for example, having thickness of 10 mm or adding an additional CZT layer of 5 mm thick above the first 5 mm thick CZT layer will result with stopping power A of: $A_{10mmCZT} 0.9 + (1-0.9) \times 0.9 = 99\%$.

As shown by Equation (1), the second 5 mm thick CZT layer contributes only an additional 9% to the total absorption while the first 5 mm thick CZT layer contributes 90% to the total absorption. This situation exists due to the fact that most of the radiation is absorbed in the first layer and only the portion left after the first layer is left to be absorbed in the second layer.

In various embodiments in accordance with the present inventive subject matter, the efficiency of a double wafer detector is improved by allowing direct access of radiation from the patient body into each of the CZT wafers, or into plural wafers or detectors positioned at various levels. It may be noted that, as used herein, a single CZT layer or multiple CZT layers may also be understood as radiation detectors that include a single CZT layer or multiple CZT layers. In various embodiments, the radiation arriving into the upper CZT detector or wafer is not first absorbed or passed through the first CZT wafer or detector. For example, the first CZT layer may receive radiation via a parallel-hole collimator, and an upper CZT layer may receive radiation directly via a pinhole in the center of the parallel-hole collimator. Accordingly, the sensitivity of the upper layer is increased relatively dramatically, and the sensitivity of the two layers combined may be increased by a factor of about 150% or more, relative to a detector including a single CZT layer, even though the area (and sensitivity) of the first layer is reduced to create the direct path for the radiation to pass via the pin-hole to the second or upper layer. In various embodiments, the positioning of the second layer at a distance above the first layer may result in a detector module having a slightly larger height than a convention module, but this added height may have a minimal effect on the rotational range of the detector module.

A technical effect provided by various embodiments includes increased sensitivity of a detector system, such as a NM imaging detector system. The detector system may be provided in a rotating head detector module that may be used as part of a group of similar rotating head detector modules in an imaging system. A technical effect of various embodiments includes allowing for a reduction in radiation dose to which a patient is exposed. A technical effect of various embodiments includes reduction in scan-time, which may provide increased convenience or reduced anxiety or discomfort for patients, and/or improved throughput time for scans, thereby improving return on investment for an operator of an imaging system.

FIGS. 1$a$-1$c$ provide schematic block diagrams of collimator assembly 100 in accordance with an embodiment. The collimator assembly 100 includes a parallel hole collimator 120 and a pin-hole collimator 150, and is configured for use with a first detector 170 and a second detector 180. The parallel hole collimator 120 is configured to control the passage of radiation from a region of interest 110 of a patient body 112 to the first detector 170, and the pin-hole collimator 150 is configured to control the passage of radiation from the region of interest 110 of the patient body 112 to the second detector 180. In the illustrated embodiment, the region of interest 110 is a surface within the patient body for which imaging data is to be obtained. The region of interest 110 is positioned a length 117 into the patient body 112. It may be noted that the patient body 112 is depicted having a rectangular shape and the region of interest 110 is shown as a generally straight line for schematic purposes and ease of illustration. Other shapes or configurations may be employed in various embodiments.

As seen in FIG. 1$a$, the parallel-hole collimator 120 includes plural walls (known also as collimator dividers or septa) 122 that define parallel holes 124. It may be noted that, in some embodiments, the walls may have a tapered or sloped design so that the holes 124, while generally parallel, may not be entirely parallel in all embodiments. The holes 124 may be understood as openings in tubes defined by the walls 122. The holes 124, for example, may have a generally square cross-section. The holes 124 may each define a parallel-hole width 125. The parallel holes 124 and walls 122 are disposed about central opening 126. In the illustrated embodiment, the central opening has a generally square-shaped cross-section having an opening width 127 in each direction. Other shapes of opening (e.g., circular, rectangular, or triangular, among others), may be utilized in alternate embodiments.

The parallel-hole collimator 120 has a height 130 extending from a bottom 132 to a top 134 of the parallel-hole collimator. The top 134 in the depicted embodiment corresponds to a detector end 118 disposed toward the first detector 170, and the bottom 132 corresponds to a source end 119 oriented toward a source of radiation (e.g., a patient body 112 having a region of interest 110). A midpoint 136 is defined as a half-way point between the bottom 132 and the top 134 of the parallel-hole collimator 120, or half-way up the height 130.

In the illustrated embodiment, the pin-hole collimator 150 is disposed within the central opening 126 proximate the midpoint 136. For example, a bottom surface of the pin-hole collimator 150 may be positioned at the midpoint 136, or at an elevation of half the height 130 from the bottom 132 of the parallel-hole collimator 120. In the illustrated embodiment, the pin-hole collimator 150 includes a body 152 and a pinhole 154 extending through the body 152. The body 152 may be comprised of a material configured to absorb or block radiation, such that radiation impinging upon the second detector 180 is substantially limited to radiation passing through the pin-hole 154. The pin-hole 154 may be, for example, square or circular shaped, and may define a pin-hole width 155. The pin-hole collimator 150 has a pin-hole collimator height 156 corresponding to the distance from the body 152 (e.g., a bottom surface of the body) to the second detector 180. Also, the depicted pin-hole collimator 150 defines a pin-hole collimator distance 158 from the body 152 to the region of interest 110.

The first detector 170 is positioned and configured to receive radiation passed through the holes 124 of the parallel-hole collimator 120. The first detector 170 has a thickness 179. The first detector 170 in the illustrated embodiment is generally square shaped, with a detector width 171. As best seen in FIG. 1b, the first detector 170 has a central opening 172, which in the illustrated embodiment is the same size as the central opening 126 of the parallel-hole collimator 120. The central opening 172 of the first detector 170 allows radiation to pass directly from the pin-hole collimator 150 to the second detector 180 without impinging upon the first detector 170.

In the illustrated embodiment of FIG. 1b, the first detector 170 is constructed from detector tiles 174. The detector tiles 174 may be CZT wafer detectors having pixels or anodes (not shown in FIG. 1b) thereon. The pixels may be sized and positioned the same as the holes 124 of the parallel-hole collimator 120 and may be registered with holes 124 in some embodiments, or have different numbers or positions than the holes 124 in other embodiments. The tiles 174 have a tile length 176 and a tile width 178.

The second detector 180 is positioned and configured to receive radiation that passes through the pin-hole 154 of the pin-hole collimator 150. The thickness and outer dimensions of the second detector 180 may be similar to that of the first detector 170 (e.g., the second detector 180 may be generally square shaped and have a width 171 that is the same as the width 171 of the first detector 170). However, as best seen in FIG. 1c, the second detector 180 is substantially solid across a cross-section, and does not have a central opening. The second detector 180 includes pixels 182 (or anodes) arranged in a grid having a pitch 184 that may be similar to the pitch of the holes 124 of the parallel-hole collimator 120.

Returning to FIG. 1c, the collimators define different fields of view. For example, each pixel of the parallel-hole collimator has a spatial resolution shown by example parallel-hole resolutions 192. The parallel-hole resolutions 192 are part of a parallel-hole field of view 194 of the parallel-hole collimator 120. An example pin-hole resolution 196 is shown for a centrally located pixel of the second detector 180. The placement of the particular pin-hole resolution 196 depicted in FIG. 1a is for a centrally located pixel 183; pixels located away from the center of the second detector 180 may have locations of spatial resolutions skewed to a side of the depicted pin-hole resolution 196. The pin-hole collimator 150 and the second detector 180 have a pin-hole field of view 198 as shown in FIG. 1a. As seen in FIG. 1a, the pin-hole field of view 198 is larger than the parallel-hole field of view 196. In various embodiments, the collimator assembly 100 may be arranged such that the pin-hole spatial resolution 196 for each pixel of the second detector 180 is the same as the parallel-hole resolution 194 for each tube or hole of the first detector 170. It may be noted that the resolutions and fields of view are shown in just one dimension in FIG. 1a, but would also extend in a second dimension into and out of the page. (For embodiments utilizing square-shaped collimators, detectors, and openings, the dimensions into and out of the page would be similar to those shown in FIG. 1a.)

The following table provides example values for various parameters of the collimator assembly 100. Different values may be utilized in different embodiments.

| Parameter | Value |
| --- | --- |
| Detector width 171 | 40 millimeters |
| Tile length 176 | 29.5 millimeters |
| Tile width 178 | 10.5 millimeters |
| Pixels pitch 184 | 2.46 millimeters |
| Central opening width 127 | 18.8 millimeters |
| Patient-body length 117 | 100 millimeters |
| Pin-hole collimator height 156 | 48 millimeters |
| Pin-hole width 155 | 2.46 millimeters |
| Pin-hole collimator distance 158 | 120 millimeters |
| Parallel-hole collimator height 130 | 40 millimeters |
| Thickness of walls 122 | 0.3 millimeters |
| Parallel-hole width 125 | 2.16 millimeter |
| Parallel-hole resolutions 192 | 7.56 millimeter |
| Pin-hole resolution 196 | 8.61 millimeter |
| Parallel-hole field of view 194 | 45.1 millimeters |
| Pin-hole field of view 198 | 108.61 millimeters |

The values provided in the table may correspond to an improvement in sensitivity of about 1.5 times provided by merely stacking an additional CZT layer on top of an existing similarly sized CZT layer. In other embodiments, the values of parameters may be selected, for example, to provide uniformity in production. For example, in some embodiments, an integer number of pixels in the tiles 174 having a pitch of about 2.5 mm may be employed. In some embodiments, the second detector 180 may include a 40 millimeters×40 millimeters square wafer (e.g., including a 16×16 grid of pixels), and the first detector 170 may define an outer envelope of 40 millimeters×40 millimeters, using tiles that are sized 15 millimeters×25 millimeters (e.g., tile length 176 is 25 millimeters and tile width 178 is 15 millimeters corresponding to a 10×6 grid of pixels).

It may be noted that the parameters of the collimators and detectors may be understood as are divided into three types of parameters. Namely, the parameters may be parameters that are fixed or generally fixed by sizes of commonly available or used components, variable parameters that may be selected to optimize system performance to address or satisfy one or more criteria, and calculated parameters that are derived from the values of other (e.g., fixed or variable as defined above) parameters.

In some embodiments, the length and width of the detectors (e.g., detector width 171) may be a fixed parameter of M=40 millimeters, where M is the length and width of the detector surface. As another example, the detector thickness (e.g., thickness 179), may be understood as $T_1$=5 millimeters, where $T_1$ is the thickness of the detector layers (e.g., thickness of CZT layers). As another example, the pitch of the pixels of the detectors (e.g., pitch 184) may be understood as P=2.46 millimeters, where P is the pitch of pixels of the detectors. As another example, the thickness of the walls 122 may be understood as $T_3$=0.3 millimeters, where $T_3$ is the thickness of walls 122. As one more example of a fixed parameter in various embodiments, the number of pixels (for the second detector 180, for example) may be N=256 (e.g., a 16×16 grid of pixels).

In various embodiments, some parameters may be variable and selected to suit a particular application. For example, in some embodiments, the collimator height (e.g., the height 130 of the pin-hole collimator 120) may be understood as $h_C$=40 millimeters, where $h_C$ is the height of the parallel-hole collimator. As another example, the size of the opening of the pin-hole (e.g., pin-hole width 155) may be understood as d=2.46 millimeters, where d is the size of the opening of the pin-hole of the pin-hole collimator. As another example, the depth of the region of interest in the patient body (e.g., the length 117) may be understood as L=100 millimeters, where L is the depth of the region of interest (e.g., region of interest 110) in the patient body (e.g., patient body 112).

Using the fixed and/or variable parameters, a number of calculated parameters may be determined. For example, the size of the opening of the collimator tubes (e.g., parallel-hole width 125) may be represented by $W_1$. The clear area of the pixel $d_1$ may be equal to the pitch P less the thickness $T_3$ of walls 122. Also, the size of the opening of the collimator center (e.g., opening width 127 of the central opening 126) may be represented by $W_2$. Further, the position of the pin-hole collimator (e.g., pin-hole collimator 150) above and below the edges of the collimator and edge of first CZT layer (e.g., the distance of the pin-hole collimator from the top 134 and bottom 132 of the parallel-hole collimator 120) may be represented by q (for the embodiment illustrated in FIG. 1, the distance of the pin-hole collimator 150 from the top 134 and from the bottom 132 is the same because the pin-hole collimator 150 is disposed at the midpoint 136)). The distance (e.g., pin-hole collimator height 156) of the second CZT layer (e.g., second detector 180) above the pin-hole collimator may be represented by $h_2$. Further, the distance front the pinhole to the region of interest (e.g., the pin-hole collimator distance 158) may be represented by $h_1$. Also, the field of view of the pin-hole (e.g., pin-hole field of view 198) may be represented by $F_p$; the field of vie of the parallel-hole collimator (e.g., parallel-hole field of view 194) may be represented by $F_c$. The spatial resolution of the pin-hole collimator (e.g., pin-hole resolution 196) may be represented by $R_p$, and the spatial resolution of the parallel-hole collimator may be represented by $R_c$. Using the above parameters, for the arrangement depicted in FIG. 1a, the calculated parameters may be determined using the following relationships:

$$d_1 = P - T_3 \qquad \text{Eq. (1)}$$

$$q = \frac{(h_c + T_1)}{2} \qquad \text{Eq. (2)}$$

$$W_1 = \frac{(2.16 \cdot h_c)}{40} \qquad \text{Eq. (3)}$$

$$R_C = \frac{[W_1 \cdot (h_C + L)]}{h_C} \qquad \text{Eq. (4)}$$

$$h_1 = L + q \qquad \text{Eq. (5)}$$

$$R_P = \frac{[d \cdot (h_1 + h_2)]}{h_2} \qquad \text{Eq. (6)}$$

$$R_P = R_C \qquad \text{Eq. (7)}$$

In Equation 7, the spatial resolution of the parallel-hole collimator and the pin-hole collimator are set to be the same. From the requirement that $R_p$=$R_c$, $h_2$ may be determined by:

$$h_2 = \frac{d \cdot h_1}{(R_C - d)} \qquad \text{Eq. (8)}$$

$$W_2 = \frac{M \cdot q}{h_2} + \frac{d \cdot (h_2 - q)}{h_2} \qquad \text{Eq. (9)}$$

The pinhole sensitivity for the upper CZT layer may be determined by:

$$S_P = \sum_{i=1,j=1}^{i=16,j=16} s_{i,j} \qquad \text{Eq. (10)}$$

$$= \sum_{i=1,j=1}^{i=16,j=16} \left( \frac{P^2}{4\pi} \cdot \frac{d^2 \cdot (\sin(\alpha_{i,j}))^3}{h_2^2} \right)_{i,j}$$

$$= \sum_{i=1,j=1}^{i=16,j=16} = \frac{P^2}{4\pi} \cdot \frac{d^2 \cdot (\sin(\alpha_{i,j}))^3}{h_2^2}$$

$$= 4 \cdot \left( \frac{P^2}{4\pi} \cdot \frac{d^2}{h_2^2} \right) \cdot \sum_{i=1,j=1}^{i=8,j=8} (\sin(\alpha_{i,j}))^3 =$$

If the pinhole is located above point (i=0, j=0) in the center of the CZT wafer, then $\alpha_{i,j}$ is given by:

$$\alpha_{i,j} = \arctan\left( \frac{h_2}{\sqrt{[p \cdot (i - 0.5)]^2 + [p \cdot (j - 0.5)^2}} \right) \qquad \text{Eq. (11)}$$

where the index i goes from 1 to 8 and the index j goes from 1 to 8.

The sensitivity of the parallel-collimator for the lower CZT layer may be given by:

$$S_C = 256 \cdot \left( \frac{W_1^2}{4\pi} \cdot \frac{W_1^2}{h_C^2} \right) \cdot \frac{(M^2 - W_2^2)}{M^2} \qquad \text{Eq. (12)}$$

The sensitivity ratio between the depicted embodiment and conventional approaches using two similarly sized stacked CZT layers may be determined by:

$$R = \frac{S_C + S_P}{S_C \frac{(M^2)}{(M^2 - W_2^2)}} = \left( \frac{S_C + S_P}{S_C} \right) \cdot \left( \frac{(M^2 - W_2^2)}{(M^2)} \right) \qquad \text{Eq. (13)}$$

This ratio may be equal to, for example, about 1.5 in various embodiments.

It may be noted that other values of parameters and/or relationships between fixed, variable, and calculated parameters may be utilized in various embodiments.

Collimator assemblies, for example the collimator assembly 100, formed in accordance with various embodiments may provide a number of benefits. For example, sensitivity may be increased. As another example, although a pin-hole collimator may be inferior in certain respects to a parallel-hole collimator in imaging quality, the information provided via a pin-hole collimator (e.g., by the second detector 180) may be used efficiently, for example, when the improved image quality of the parallel-hole collimator is used utilizing Most Likelihood Expectation Maximization (MLEM) techniques to process the information provided via the pin-hole collimator (e.g., via the second detector 180). Further, by adding a pin-hole collimator, less overlapping between voxels may be achieved (e.g., for the second detector 180). Further still, additional viewing angles may be provided, and/or a larger field of view provided to help reduce or eliminate blind spots that may occur between rotating detector heads as the rotating detector heads pivot or swing.

FIG. 2 illustrates a detector head assembly 200 formed in accordance with various embodiments. The detector head assembly 200, for example, may be configured as a rotating head detector assembly. The rotating head detector assembly may be pivotally attached to a telescoping arm (not shown in FIG. 2). The detector head assembly 200 includes a parallel-hole collimator 210 (e.g., parallel-hole collimator 120), a pin-hole collimator 220 (e.g., pin-hole collimator 150 of FIG. 1), a first detector 230 (e.g., first detector 170) that receives radiation collimated by the parallel-hole collimator 210, and a second detector 240 (e.g., second detector 180) that receives radiation collimated by the pin-hole collimator 220. The detector head assembly 200 also includes a first analog front end (AFE) 250 and a second AFE 260, as well as a digital readout board (DRB) 270. The first AFE 250 is operably coupled to the first detector 230, and the second AFE 260 is operably coupled to the second detector 240. For example, the first AFE 250 may have a similarly sized central opening as the first detector 230 and the pin-hole collimator 210. Each AFE in the illustrated embodiment is configured as a printed board directly attached to the corresponding detector. The DRB 270 is operably coupled to the first AFE 250 and the second AFE 260. The DRB 270 may be understood as a common DRB for the first AFE 250 and the second AFE 260 (and/or for the first detector 230 and the second detector 240).

Figure 3:
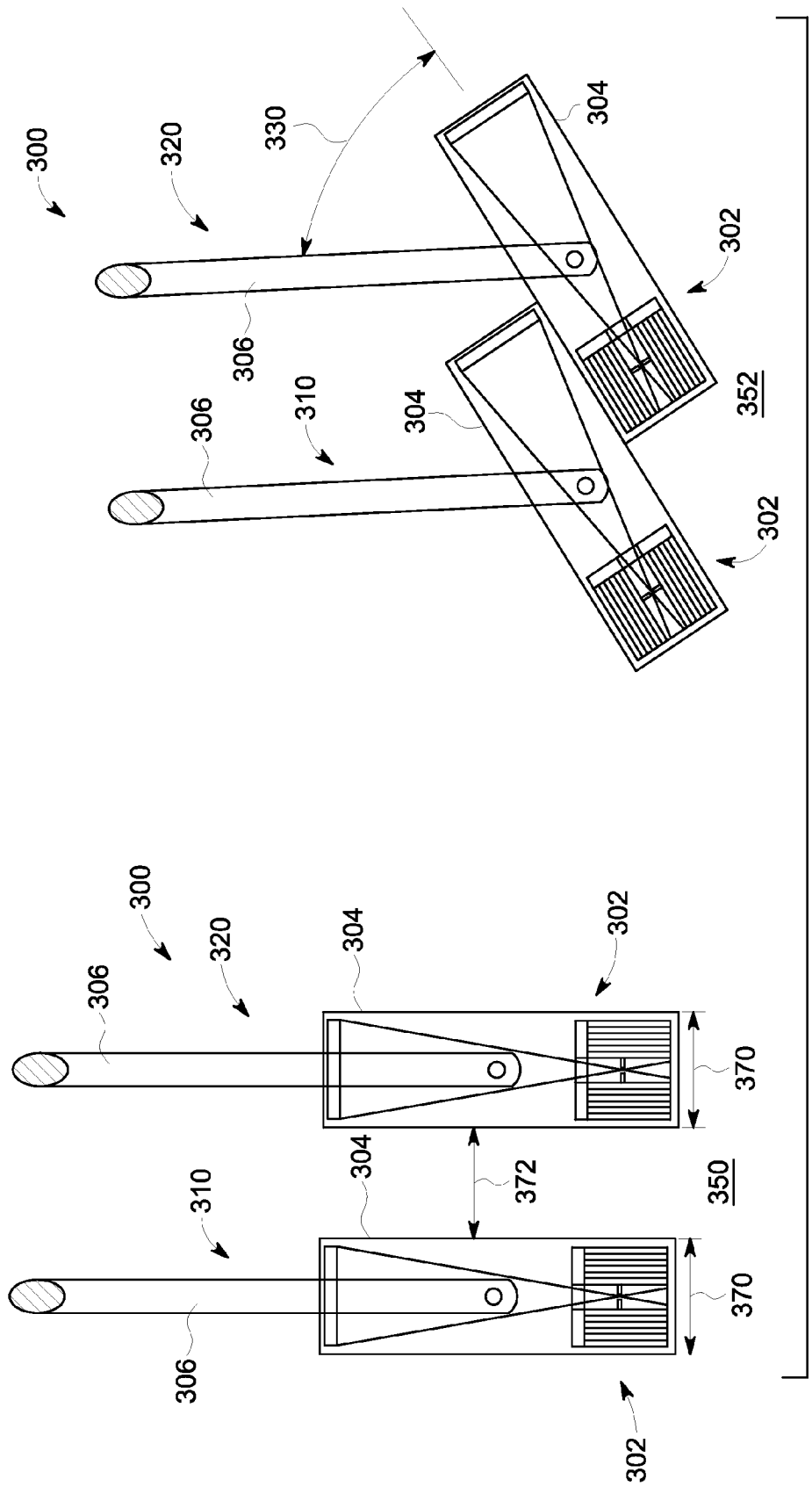
FIG. 3 is a diagram illustrating rotation of detector heads in accordance with various embodiments.

As mentioned above, the collimators and detectors, for example of FIGS. 1 and/or 2 may be employed as part of a rotating head detector module or assembly. FIG. 3 illustrates a schematic view of an imaging system 300 formed in accordance with various embodiments in a first position 350 and a second position 352. The imaging system 300 includes a first detector head 310 and a second detector head 320. The detector heads have a width 370 are spaced from each other a distance 372 that is equal to the width. Other spacings and/or widths may be employed in various embodiments. Each detector head shown in FIG. 3 includes a collimator assembly 302 that may be substantially similar to the collimator assembly 100 discussed herein. Each detector head includes a body 304 pivotally attached to an arm 306. The arm 306 may be a telescoping arm in various embodiments. As the pin-hole collimator of the depicted example is disposed at a distance from the parallel-hole collimator, the depicted detector heads may have an increased height relative to a conventional device utilizing detector directly stacked on top of each other. However, as shown in the example of FIG. 3, the rotating head detectors 310, 320 may still be capable of a significant rotation. For example, in the illustrated embodiment, the rotating head detectors 310, 320 may rotate through an angle 330 of about 60 degrees in the second position 352 relative to the first position 350 before contacting one another. The arrangement of FIG. 3 is limited to 2 detector heads arranged generally linearly for simplicity and clarity of illustration. It may be noted that additional detector heads and/or other arrangements of detector heads may be utilized in various embodiments.

In various embodiments, rotating head detector assemblies may be provided including one or more detector heads each pivotally connected to a corresponding arm (e.g., telescoping arm). Each detector head may include plural NM imaging detectors configured to receive radiation from a source (e.g., patient body), with each NM imaging detector receiving radiation directly from the source over at least a portion of the NM imaging detector. The detector assemblies may include at least one pin-hole collimator positioned to collimate radiation received by at least one of the NM imaging detectors. The collimator assembly 100 of FIG. 1 (as well as collimator assembly 302 of FIG. 3, for example) is an example of such an arrangement, as each of the first detector 170 and second detector 180 receive radiation directly (e.g., radiation that has not previously passed through a different detector or wafer) from the radiation source (e.g., patient body 112). FIGS. 4-9 provide additional examples of rotating head detectors including plural NM imaging detectors that receive radiation directly from a source, although being placed at different levels or orientations. It may be noted that the detectors in FIG. 1 are arranged parallel to each other, but that detectors in other arrangements may not be oriented parallel to one another. It may further be noted that, in various embodiments, edges or sides of parallel-hole collimators may be configured to act as pin-holes for pin-hole collimators (e.g., one or more parallel-hole collimators may cooperate with other structure to form a body and/or pin-hole of a pin-hole collimator).

Figure 4:
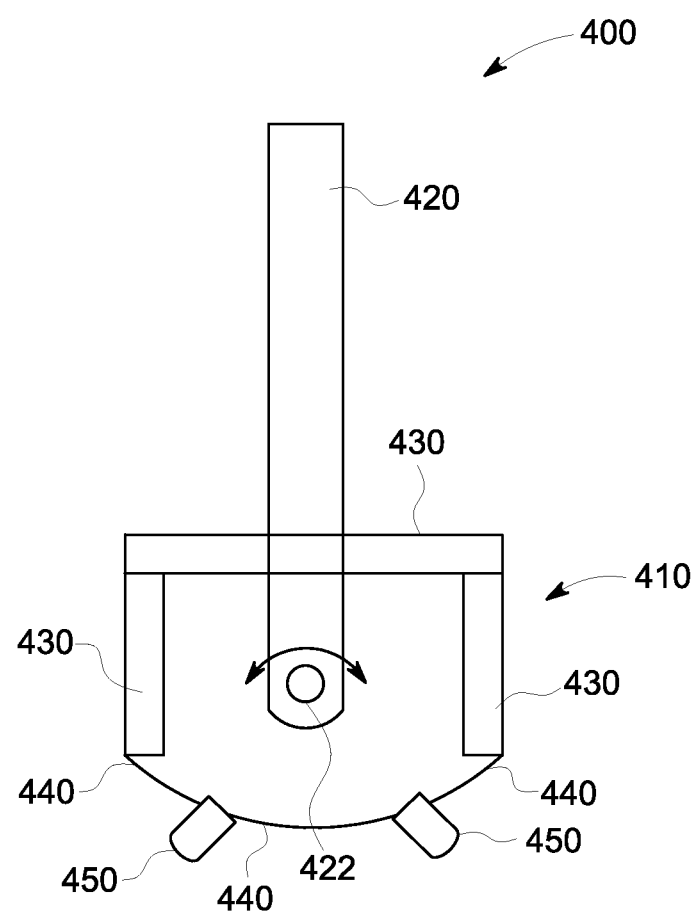
FIG. 4 is a diagram illustrating a detector assembly in accordance with various embodiments.

FIG. 4 provides a schematic view of a detector assembly 400 formed in accordance with various embodiments. The detector assembly 400 includes a head 410 pivotally joined to an arm 420 to pivot about an axis of rotation 422. The head 410 includes detectors 430 (e.g., CZT detectors) arranged in a generally "U" shaped configuration. The detector assembly 400 includes shielding 440, and pin-holes 450 extending through the shielding 440 to provide pin-hole collimator from the pin-holes 450. Each detector 430 receives direct radiation from at least one pin-hole 450 over at least a portion of the detector surface. In FIG. 4, each detector 430 is at a non-parallel orientation to at least one other detector 430, and all collimation is provided via pin-holes.

Figure 5:
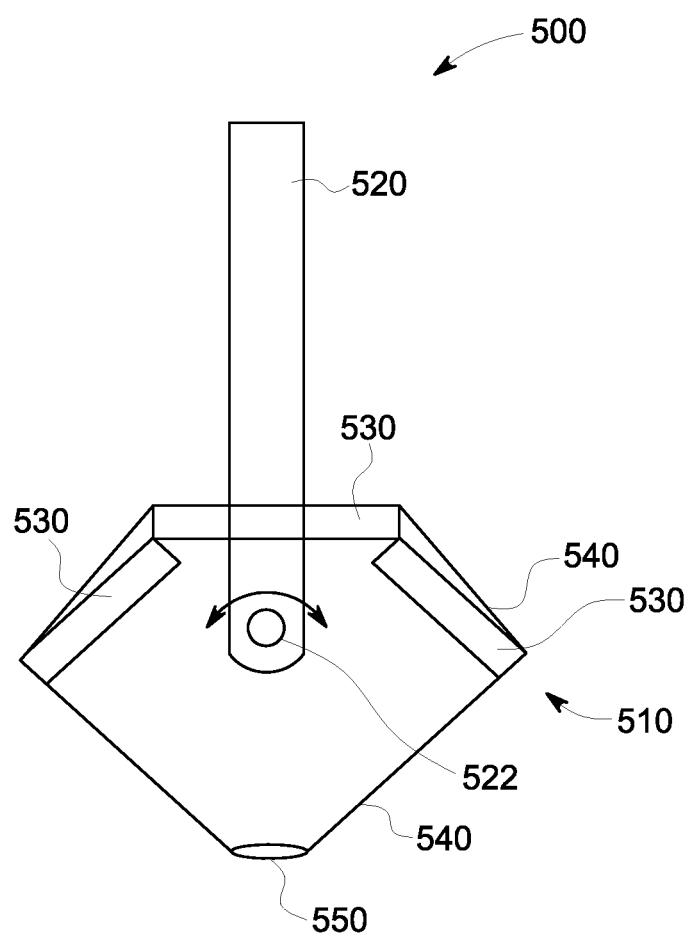
FIG. 5 is a diagram illustrating another detector assembly in accordance with various embodiments.

FIG. 5 provides a schematic view of a detector assembly 500 formed in accordance with various embodiments. The detector assembly 500 includes a head 510 pivotally joined to an arm 520 to pivot about an axis of rotation 522. The head 510 includes detectors 530 (e.g., CZT detectors) arranged as shown in FIG. 5. The detector assembly 500 includes shielding 540, and a single pin-hole 550 extending through the shielding 540 to provide pin-hole collimator for the detectors 530 from the pin-hole 550. Each detector 530 receives direct radiation from the pin-hole 550 over at least a portion of the detector surface. In FIG. 5, each detector 530 is at a non-parallel orientation to at least one other detector 530, and all collimation is provided via a single pin-hole. The detectors at the sides of the detector head may be understood to be positioned at a first level or layer, and the detector in the middle of the detector head may be understood to be positioned at a second level or layer. As shown in FIG. 5, detectors at different levels or layers may receive radiation via a single pin-hole (e.g., pin-hole 550). For example, in the illustrated embodiment, the detectors positioned at the side define an opening through which radiation may reach at least a portion of the detector in the middle (in the second layer).

Figure 6:
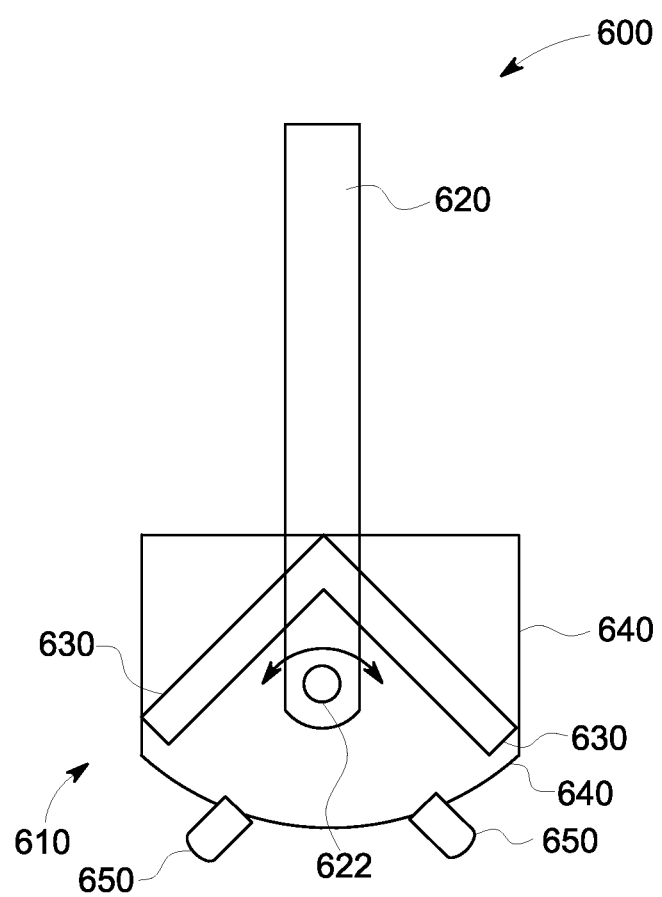
FIG. 6 is a diagram illustrating another detector assembly in accordance with various embodiments.

FIG. 6 provides a schematic view of a detector assembly 600 formed in accordance with various embodiments. The detector assembly 600 includes a head 610 pivotally joined to an arm 620 to pivot about an axis of rotation 622. The head 610 includes detectors 630 (e.g., CZT detectors) arranged in a generally "V" or "L" shaped configuration. The detector assembly 600 includes shielding 640, and pin-holes 650 extending through the shielding 640 to provide pin-hole collimator from the pin-holes 650. Each detector 630 receives direct radiation from at least one pin-hole 650 over at least a portion of the detector surface. In FIG. 6, each detector 630 is at a non-parallel orientation to at least one other detector 630, and all collimation is provided via pin-holes. The lower portions of detectors 630 at the sides of the detector head 610 may be understood to be positioned at a first level or layer, and the upper portions of detectors 630 in the middle of the detector head may be understood to be positioned at a second level or layer.

Figure 7:
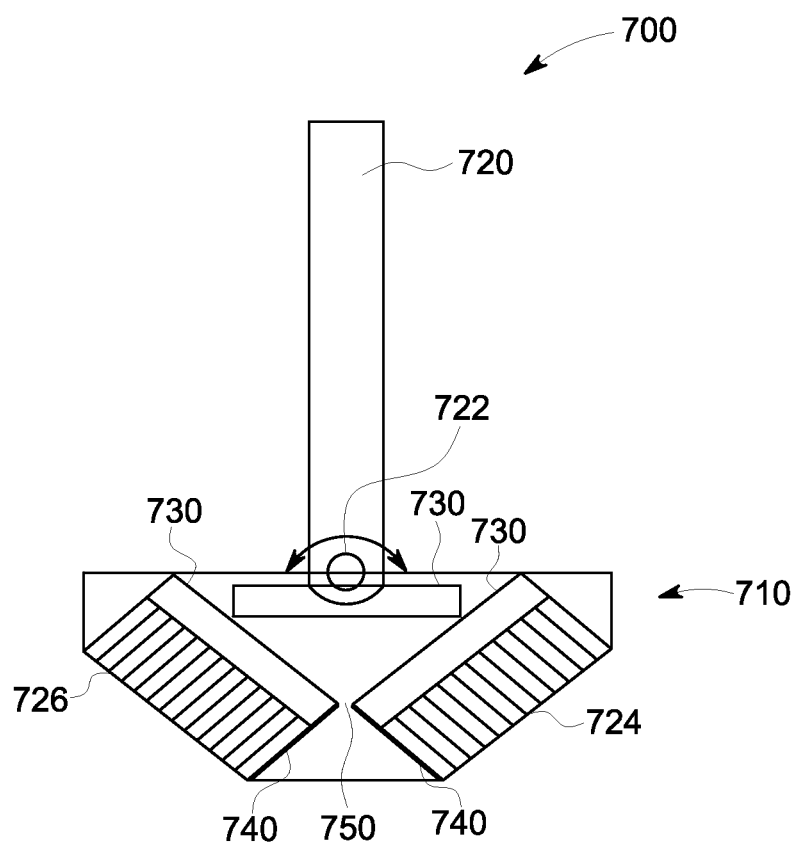
FIG. 7 is a diagram illustrating another detector assembly in accordance with various embodiments.

FIG. 7 provides a schematic view of a detector assembly 700 formed in accordance with various embodiments. The detector assembly 700 includes a head 710 pivotally joined to an arm 720 to pivot about an axis of rotation 722. The head 710 includes detectors 730 (e.g., CZT detectors) arranged as shown in FIG. 7. The detector assembly 700 includes two parallel-hole collimators 724, 726 arranged to form a pin-hole 750. The parallel-hole collimators 724, 726 provide parallel-hole collimation for the detectors 730 oriented toward the sides of the detector assembly 700, while the pin-hole 750 provides pin-hole collimation for the detector 730 positioned centrally in the head 710. The detector assembly 700 includes shielding 740 disposed on sides of the parallel-hole collimators 724, 726 and associated detectors to form the pin-hole 750. Each detector 730 receives direct radiation over at least a portion of the detector surface. In FIG. 7, each detector 730 is at a non-parallel orientation to at least one other detector 730, and collimation is provided via both pin-hole and parallel-hole collimation. The detectors 730 at the sides of the detector head 710 that are attached to parallel-hole collimators 724 and 726 may be understood to be positioned at a first level or layer, and the detector 730 positioned above pinhole 750 in the middle of the detector head may be understood to be positioned at a second level or layer.

Figure 8:
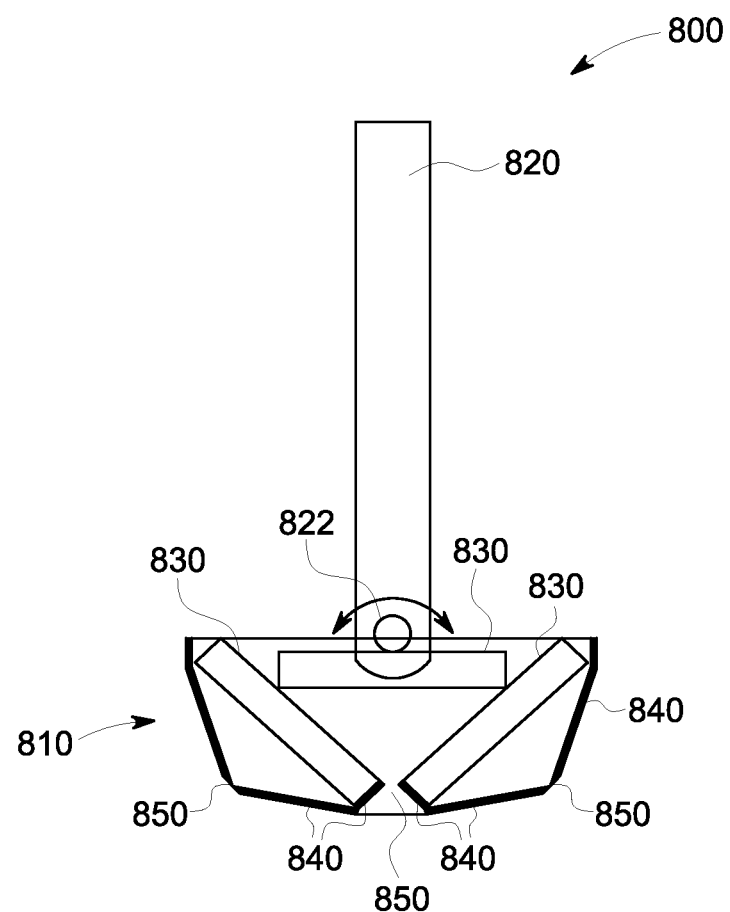
FIG. 8 is a diagram illustrating another detector assembly in accordance with various embodiments.

FIG. 8 provides a schematic view of a detector assembly 800 formed in accordance with various embodiments. The detector assembly 800 includes a head 810 pivotally joined to an arm 820 to pivot about an axis of rotation 822. The head 810 includes detectors 830 (e.g., CZT detectors) arranged as shown in FIG. 8. The detector assembly 800 includes shielding 840 to provide pin-holes 850. The centrally disposed pin-hole is formed at least in part using shielding 840 on the two detectors 830 oriented toward the side of the detector head 810. Each detector 830 receives direct radiation over at least a portion of the detector surface. In FIG. 8, each detector 830 is at a non-parallel orientation to at least one other detector 730, and all collimation is provided via pin-hole collimation. The detectors 830 at the sides of the detector head 810 may be understood to be positioned at a first level or layer, and the detector 830 positioned above central pinhole 850 in the middle of the detector head may be understood to be positioned at a second level or layer.

Figure 9:
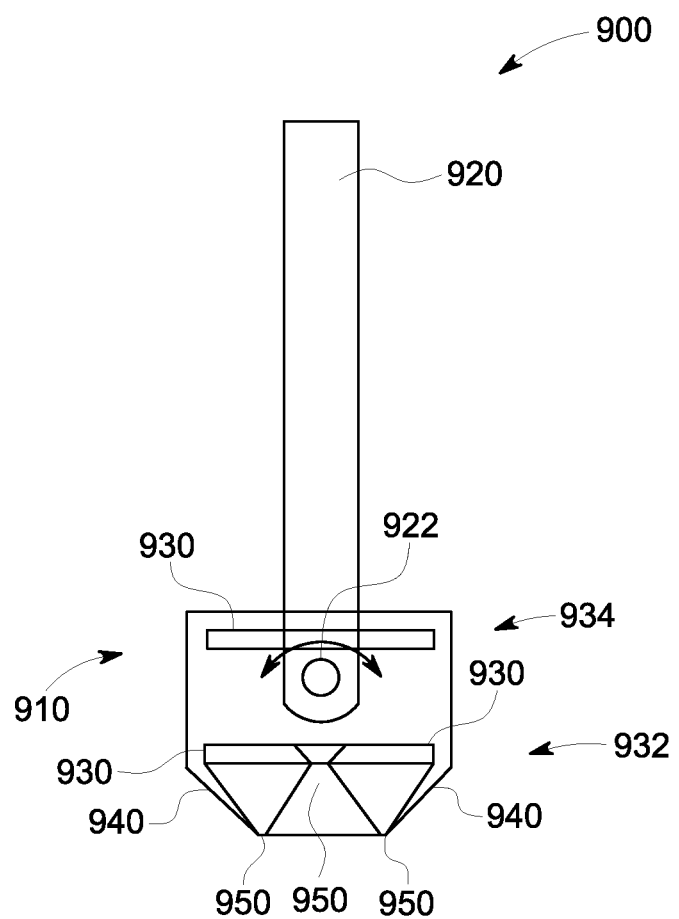
FIG. 9 is a diagram illustrating another detector assembly in accordance with various embodiments.

FIG. 9 provides a schematic view of a detector assembly 900 formed in accordance with various embodiments. The detector assembly 900 includes a head 910 pivotally joined to an arm 920 to pivot about an axis of rotation 922. The head 910 includes detectors 930 (e.g., CZT detectors) arranged as a first layer 932 and a second layer 934 as shown in FIG. 9. The detector assembly 900 includes shielding 940, and pin-holes 950 extending through the shielding 940 to provide pin-hole collimator from the pin-holes 950. Each detector 930 receives direct radiation from at least one pin-hole 950 over at least a portion of the detector surface. In FIG. 9, each detector 930 is oriented in a substantially parallel orientation to at least one other detector 930, and all collimation is provided via pin-holes.

Figure 10:
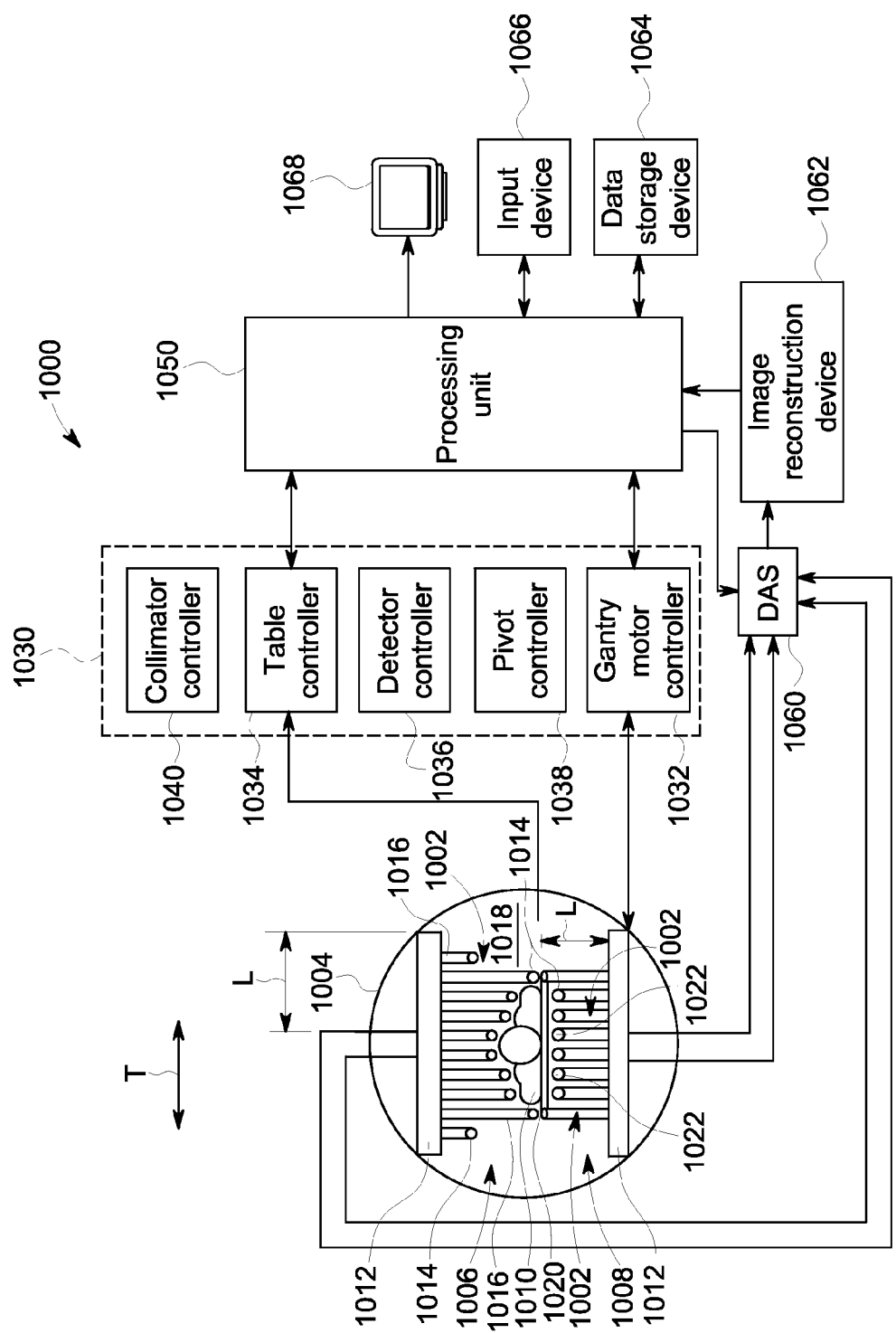
FIG. 10 is a schematic block diagram of a Nuclear Medicine (NM) imaging system in accordance with an embodiment.

FIG. 10 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). In particular, a plurality of imaging detectors 1002 are mounted to a gantry 1004. Each detector 1002 may include, for example, collimators and detectors arranged generally similarly to the arrangements discussed in connection with FIGS. 1-9. In the illustrated embodiment, the imaging detectors 1002 are configured as two separate detector arrays 1006 and 1008 coupled to the gantry 1004 above and below a subject 1010 (e.g., a patient), as viewed in FIG. 1. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 10). Additionally, each of the imaging detectors 1002 includes a detector unit 1014 (which may include collimator and/or detector assemblies as discussed herein in connection with FIGS. 1-9), at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels. In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 10 are depicted for ease of illustration as single collimators in each detector head. However, it should be noted that the collimators 1022 may be configured according to various embodiments discussed herein, such as the embodiments discussed in connection with FIG. 1-9. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator. As discussed herein, in some embodiments both parallel-hole and pin-hole collimation may be employed. As another example, in some embodiments, only pin-hole collimation may be employed.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially as described in more detail herein.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually as described in more detail herein. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022, as shown for example in FIG. 3, or as shown by detector 410 in FIG. 4, as another example. In some embodiments, detectors 1002 and collimators 1022 may swivel or rotate around an axis such as axis 422 of FIG. 4.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 10 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

Figure 11:
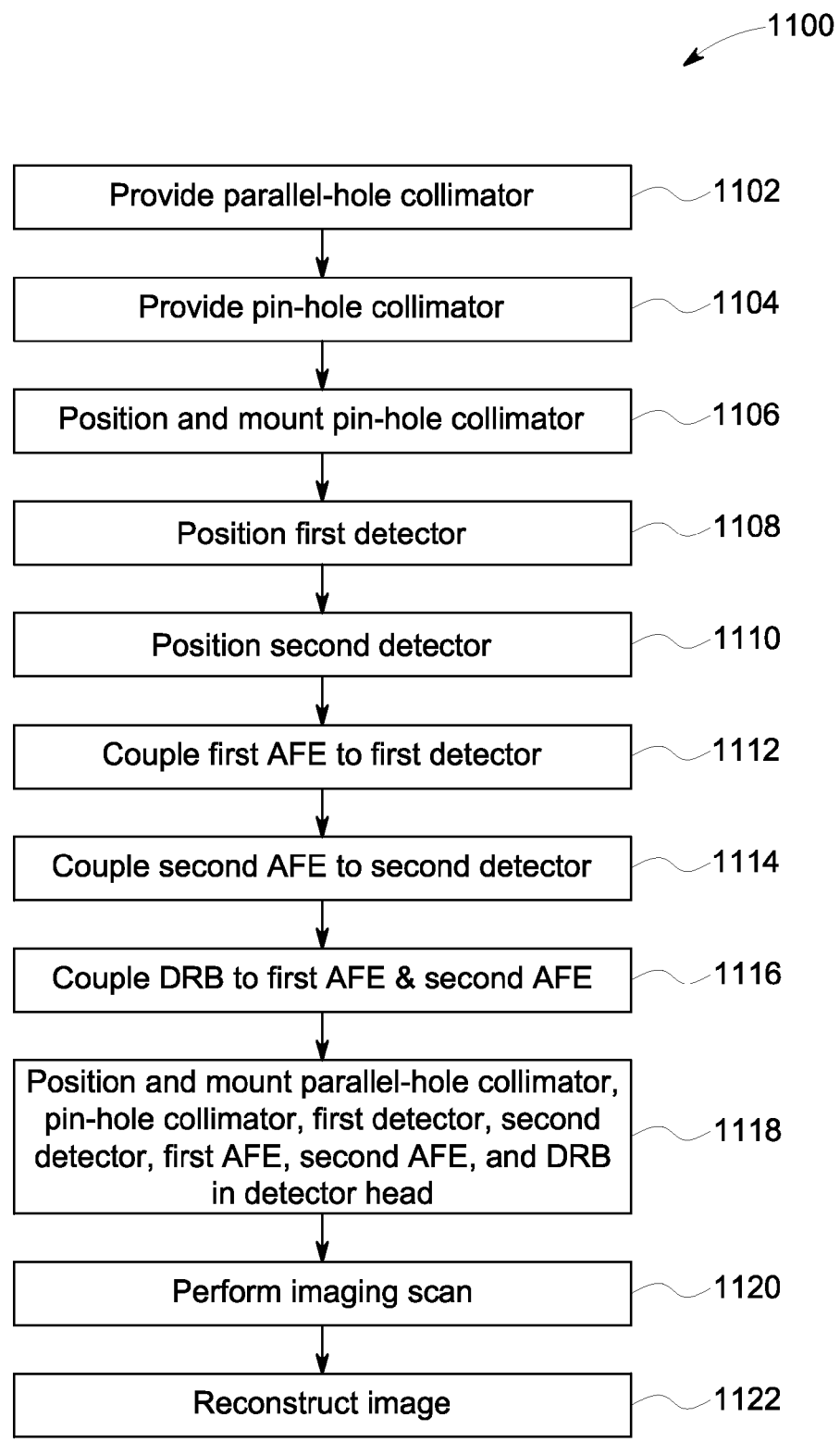
FIG. 11 is a flowchart of a method in accordance with various embodiments.

FIG. 11 provides a flowchart of a method 1100 for providing a collimator assembly in accordance with various embodiments. The method 1100, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1100 may be able to be used as one or more algorithms to direct hardware to perform one or more operations described herein.

At 1102, a parallel-hole collimator (e.g., parallel-hole collimator 120) is provided. In some embodiments, the parallel-hole collimator may include plural walls defining parallel holes therebetween, with the parallel holes arranged around a central opening.

At 1104, a pin-hole collimator (e.g., pin-hole collimator 150 of FIG. 1) is provided. It may be noted that in some embodiments, only pin-hole collimators may be provided. As another example, varying numbers of pin-hole and/or parallel-hole collimators may be provided in different embodiments. In some embodiments, one or more collimators or detectors may be provided and oriented at a non-parallel angle to one or more associated collimators or detectors.

At 1106, the pin-hole collimator 150 is positioned and mounted, for example in the central opening of the parallel-hole collimator. For example, in some embodiments, the pin-hole collimator may be mounted proximate a midpoint of the height of the parallel-hole collimator.

At 1108, a first detector is positioned. In various embodiments, the first detector is positioned proximate a detector end of the parallel-hole collimator, and is positioned and configured to receive radiation passed through the parallel holes of the parallel-hole collimator. The first detector, for example, may be mounted directly to the parallel-hole collimator, and may include a central opening matching or corresponding to the central opening of the parallel-hole collimator. In some embodiments, the pixels of the first detector may align with and correspond on a 1:1 basis with the holes of the parallel-hole collimator, while in other embodiments the pixels of the first detector may not align and/or correspond on a 1:1 basis with the holes of the parallel-hole collimator.

At 1110, a second detector is positioned. The second detector, for example, may be spaced a distance away (e.g., above) from the pin-hole collimator (as well as a distance away from (e.g., above) the parallel-hole collimator.

At 1112, a first AFE is coupled to the first detector. The first AFE, for example, may be attached directly to the first detector, and may include a central opening corresponding to or matching the central openings of the first detector and the parallel-hole collimator. The first AFE may be a printed board attached directly to the first detector.

At 1114, a second AFE is coupled to the second detector. The second AFE, for example, may be attached directly to the second detector. The second AFE may be a printed board attached directly to the second detector.

At 1116, a DRB is coupled to the first AFE and second AFE. The DRB thus may be understood as shared by or common to the first AFE and second AFE (and/or shared by or common to the first detector and second detector). The DRB is configured to provide digital outputs corresponding to information provided by the first AFE and second AFE. The information provided by the DRB may be used to reconstruct an image.

At 1118, the parallel-hole collimator, pin-hole collimator, first and second detectors, first and second AFE's, and DRB are positioned in a detector head. The detector head may be a rotating detector head. Further, a plurality of similarly structured detector heads may be provided as part of one or more arrays of detector heads in an imaging system. The detector heads, for example, may be configured to acquire SPECT information during a SPECT scan.

At 1120, an imaging scan is performed. In some embodiments, the imaging scan may be performed using plural SPECT detector units disposed around a bore of a gantry, with the plural detector units positioned proximate to surfaces of the object to be imaged (e.g., a portion of a patient). In some embodiments the detector units may be translated laterally and vertically (e.g., with respect to a vertical and horizontal plane defined by a patient bed), while the detector units may be translated radially in other embodiments to position the detector units proximate the object to be scanned. A swiveling motion of one or more detectors may be performed as well around a pivot axis. It may be noted that during the scan, imaging information may be provided and organized based on the type of collimation and/or the position coordinates of the detectors. For example, information from one or more parallel-hole collimators may be processed a first way corresponding to identifying the location of photons based on parallel hole collimation, and information from one or more detectors associated with one or more pin-hole collimators may be processed a second way corresponding to identifying the location of photons based on pin-hole collimation. In some embodiments, information from the parallel-hole collimation may be used to improve processing of information obtained via pin-hole collimation (e.g., via MLEM techniques).

At 1122, an image is reconstructed. The image may be reconstructed using information obtained during the imaging scan. Information from other scans (e.g., a scout scan or other modality scan) may be used in some embodiments. It may be noted that imaging techniques such as binning or gating, among others, may be employed in various embodiments.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A collimator assembly including:
    a parallel-hole collimator including plural walls defining parallel holes therebetween, the parallel holes arranged around a central opening; and
    a pin-hole collimator including a pin-hole formed in a body, the pin-hole collimator disposed within the central opening.

2. The collimator assembly of claim 1, wherein the plural walls define a height extending from a bottom of the plural walls to a top of the plural walls, wherein the pin-hole collimator is disposed within the central opening proximate a midpoint of the height.

3. The collimator assembly of claim 1, wherein the central opening has a generally square-shaped cross-section.

4. The collimator assembly of claim 1, further comprising a first detector positioned to receive radiation passed through the parallel-holes of the parallel-hole collimator and a second detector positioned to receive radiation passed through the pin-hole collimator, the first detector including a detector central opening corresponding to the central opening of the parallel-hole collimator, the first detector disposed proximate a detector end of the parallel-hole collimator, the second detector spaced a distance from the detector end of the parallel-hole collimator.

5. The collimator assembly of claim 4, wherein the second detector is solid across a cross-section and does not have an opening.

6. The collimator assembly of claim 4, wherein the second detector is positioned a distance $h_2$ above the pin-hole collimator, where $h_2=(d*h_1)/(R_C-d)$ where d is a size of the pin-hole of the pin-hole collimator, $h_1$ is a distance from the pin-hole to a region of interest to be imaged, and $R_C$ is a spatial resolution of the parallel-hole collimator.

7. The collimator assembly of claim 6, wherein the plural walls define a height extending from a bottom of the plural walls to a top of the plural walls, wherein the pin-hole collimator is disposed within the central opening proximate a midpoint of the height.

8. The collimator assembly of claim 1, wherein the parallel-hole collimator has a first spatial resolution and the pin-hole collimator has a second spatial resolution, wherein the first spatial resolution and the second spatial resolution are about the same.

9. A rotating head detector assembly comprising:
an arm; and
a detector head pivotally attached to the arm, the detector head configured to be directed toward a source, the detector head comprising:
plural nuclear medicine (NM) imaging detectors configured to receive radiation from the source, each NM imaging detector positioned to receive radiation directly from the source over at least a portion of the NM imaging detector; and
at least one pin-hole collimator positioned to collimate radiation received by at least one of the NM imaging detectors; and
a parallel-hole collimator including plural walls defining parallel holes therebetween, the parallel holes arranged around a central opening, wherein the at least one pin-hole collimator includes a pin-hole formed in a body, the at least one pin-hole collimator disposed within the central opening.

10. The rotating head detector assembly of claim 9, wherein the plural walls define a height extending from a bottom of the plural walls to a top of the plural walls, wherein the pin-hole collimator is disposed within the central opening proximate a midpoint of the height.

11. The rotating head detector assembly of claim 9, wherein the central opening has a generally square-shaped cross-section.

12. The rotating head detector assembly of claim 9, wherein the NM imaging detectors comprise a first detector positioned to receive radiation passed through the parallel holes of the parallel-hole collimator and a second detector positioned to receive radiation passed through the pin-hole collimator, the first detector including a detector central opening corresponding to the central opening of the parallel-hole collimator, the first detector disposed proximate a detector end of the parallel-hole collimator, the second detector spaced a distance from the detector end of the parallel-hole collimator.

13. The rotating head detector assembly of claim 6, wherein the parallel-hole collimator has a first spatial resolution and the pin-hole collimator has a second spatial resolution, wherein the first spatial resolution and the second spatial resolution are about the same.

14. The rotating head detector assembly of claim 9, wherein at least some of the NM imaging detectors are not parallel to each other.

15. The rotating head detector assembly of claim 9, wherein at least one NM imaging detector is positioned between the source and a portion of at least one other NM imaging detector.

16. The rotating head detector assembly of claim 9, further comprising at least two parallel hole collimators including plural walls defining parallel holes therebetween, wherein an opening for the at least one pin-hole collimator is formed by sides of the at least two parallel hole collimators.

17. A method comprising:
providing a parallel-hole collimator including plural walls defining parallel holes therebetween, the parallel holes arranged around a central opening;
providing a pin-hole collimator including a pin-hole formed in a body;
positioning the pin-hole collimator within the central opening of the parallel-hole collimator to form a collimator assembly.

18. The method of claim 17, further comprising:
positioning a first detector proximate a detector end of the parallel-hole collimator, the first detector positioned and configured to receive radiation passed through the parallel holes of the parallel-hole collimator, the first detector including a detector central opening corresponding to the central opening of the parallel-hole collimator; and
positioning a second detector a distance from the detector end of the parallel-hole collimator, the second detector configured to receive radiation passed through the pin-hole collimator.

19. The method of claim 18, further comprising:
operably coupling a first analog front end (AFE) to the first detector; and
operably coupling a second AFE to the second detector.

20. The method of claim 19, further comprising operably coupling a shared digital readout board (DRB) to the first AFE and the second AFE.

21. The method of claim 18, further comprising positioning the collimator assembly in a rotating head detector unit.

22. The method of claim 17, further comprising positioning the pin-hole collimator within the central opening proximate a midpoint of a height of the parallel-hole collimator.

* * * * *